(12) United States Patent
Kodama et al.

(10) Patent No.: US 7,057,067 B2
(45) Date of Patent: Jun. 6, 2006

(54) PROCESS FOR THE PREPARATION OF 2-HALOBENZOIC ACIDS

(75) Inventors: Hiroki Kodama, Sakai (JP); Takeshi Katsuhira, Kawachinagano (JP); Tateki Nishida, Tondabayashi (JP); Tomokazu Hino, Tondabayashi (JP); Kenji Tsubata, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 10/258,478

(22) PCT Filed: Apr. 27, 2001

(86) PCT No.: PCT/JP01/03707

§ 371 (c)(1),
(2), (4) Date: May 29, 2003

(87) PCT Pub. No.: WO01/83421

PCT Pub. Date: Nov. 8, 2001

(65) Prior Publication Data
US 2003/0181759 A1 Sep. 25, 2003

(51) Int. Cl.
C07C 63/04 (2006.01)
C07D 239/00 (2006.01)
C07D 213/40 (2006.01)

(52) U.S. Cl. .................. 562/493; 544/242; 546/265

(58) Field of Classification Search ................ 562/493; 564/161; 544/242; 546/265

See application file for complete search history.

(56) References Cited

U.S. PATENT DOCUMENTS 4,221,815 A 9/1980 Weyer et al.

FOREIGN PATENT DOCUMENTS

| GB | 1 163 236 | 9/1969 |
|----|-----------|--------|
| HU | 174325 | 3/1975 |
| JP | A-5-51348 | 3/1993 |
| JP | 8073403 | 3/1996 |

Primary Examiner—Cecilia J. Tsang
Assistant Examiner—Taylor Victor Oh
(74) Attorney, Agent, or Firm—Paul E. White, Jr.; Manelli Denison & Selter PLLC

(57) ABSTRACT

The present invention provides a process for producing 2-halobenzoic acids of the general formula (I), characterized by reacting a benzoic acid of formula (II) with a halogenating agent in the presence of Pd catalyst:

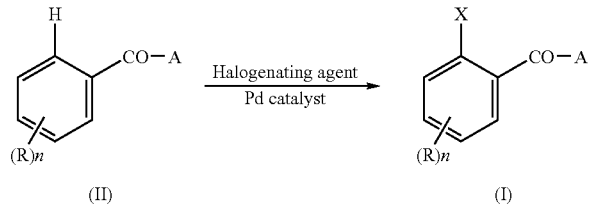

(wherein A is —OH, —OM (M is alkali metal), —N($R^6$)$R^7$ ($R^6$ and $R^7$ are each H, $C_1$–$C_6$ alkyl, optionally substituted phenyl, or the like); R is H, $C_1$–$C_6$ alkyl, $C_1$–$C_6$ alkylcarbonyl, carboxyl, $C_1$–$C_{12}$ alkoxycarbonyl, optionally substituted phenylcarbonyl, or the like; n is 0 to 4; X is Cl, Br or I, or alternatively (R)n may be present on benzene-constituting carbon atoms adjacent to each other and form a $C_3$–$C_4$ alkylene- or $C_3$–$C_4$ alkenylene-fused ring).

5 Claims, No Drawings

PROCESS FOR THE PREPARATION OF 2-HALOBENZOIC ACIDS

TECHNICAL FIELD

The present invention relates to a process for producing 2-halobenzoic acids useful as a starting material for the manufacture of pharmaceuticals and pesticides.

BACKGROUND ART

2-Halobenzoic acids are important as starting material for the manufacture of pharmaceuticals and pesticides. As processes for producing 2-halobenzoic acids, the following have been disclosed so far: (1) a process of subjecting a 2-aminobenzoic acid to Sandmeyer reaction (J. Am. Chem. Soc., 1923, 51, 1971), (2) a process of utilizing the lithiation of a benzoic acid by the use of an alkyllithium (J. Org. Chem., 1989, 54, 4372), (3) a process of using iodine-fuming sulfuric acid (Org. Synth., III, 796 (1955)), and (4) a process of using thallium (III) trifluoroacetate (J. Am. Chem. Soc., 2176 (1970), etc. Apart from above, there is known a process of introducing a halogen atom into benzene ring by the use of a palladium catalyst. In this process, however, the substrate must have (5) a functional group in which a hetero atom such as nitrogen atom or the like is directly linked to a benzene ring as a substituent, as mentioned in J. Chem. Soc. Commun., 1970, 417 or (6) a functional group in which a hetero atom is attached to the benzyl position as a substituent as mentioned in J. Organometal. Chem., 262, C11 (1984), and these processes mostly require to use a stoichiometric amount of palladium. Although some of these processes requires to use palladium only in a catalytic amount, the "catalytic amount" referred to therein is not so small but it is still as large as about 5–20% based on the amount of substrate. On the other hand, there is also known (7) a process of introducing a carbon-substituent group into benzene ring of benzoic acids substrates by the use of a palladium catalyst, as mentioned in J. Org. Chem., 1998, 63, 5211, however, no case of halogenation is reported in this type of reactions, and a catalyst cycle can be formed only by combining a copper salt with oxygen.

All these processes, however, are disadvantageous in that the process (1) entails a danger of explosion and forms a large quantity of acidic waste water; the process (2) requires a low temperature of 0° C. or below; the process (3) forms a large quantity of sulfuric acid as waste water and is insufficient in the regioselectivity; the process (4) requires to use the highly toxic metal at least in an equivalent amount to the starting material; the processes (5) and (6) are not applicable to benzoic acids or require to use an expensive palladium catalyst in a large amount, and the process (7) is not applicable to catalytic halogenation.

As above, all the prior processes have been industrially disadvantageous from the viewpoint of safety or because of the problem of waste water, or have been unable to realize halogenation at the specific position of benzoic acid. Thus, it is an object of the present invention to establish a process for regioselective halogenation reaction which allows the reaction to progress under mild conditions by the use of a catalytic amount of metal.

With the aim of solving the above-mentioned problem, the present inventors conducted extensive studies. As a result, a regioselective halogenation was achieved by reacting a benzoic acid or its derivative represented by general formula (II) with a halogenating agent in the presence of a catalytic amount of palladium catalyst, in the presence or absence of an appropriate inert solvent. Based on the result mentioned above, the present invention was accomplished.

DISCLOSURE OF THE INVENTION

Thus, the present invention relates to a process for producing a 2-halobenzoic acid represented by general formula (I):

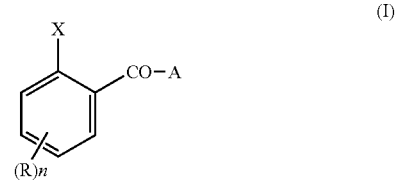

(I)

{wherein X represents a chlorine atom, a bromine atom or an iodine atom;

A represents —OH, —OM (in this formula, M represents an alkali metal atom) or —N($R^6$)$R^7$ (in this formula, $R^6$ and $R^7$ which may be the same or different represent a hydrogen atom; a $C_1$–$C_6$ alkyl group; a phenyl group; a phenyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group, halo $C_1$–$C_6$ alkoxy group, $C_1$–$C_6$ alkylsulfinyl group and $C_1$–$C_6$ alkylsulfonyl group; a group represented by the following formula:

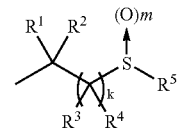

(in this formula, $R^1$, $R^2$, $R^3$ and $R^4$ which may be the same or different represent a hydrogen atom or a $C_1$–$C_6$ alkyl group, $R^5$ represents a $C_1$–$C_6$ alkyl group, m represents an integer of 0 or 1, and k represents an integer of 1 or 2); a group represented by the following formula:

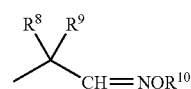

(in this formula, $R^8$, $R^9$ and $R^{10}$ which may be the same or different represent a hydrogen atom or a $C_1$–$C_6$ alkyl group); or a group represented by the following formula:

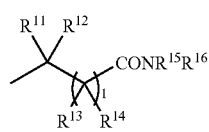

(in this formula, $R^{11}$, $R^{12}$, $R^{13}$, $R^{14}$, $R^{15}$ and $R^{16}$ which may be the same or different represent a hydrogen atom or a $C_1$–$C_6$ alkyl group and l represents an integer of 1 or 2);

R which may be the same or different represents a hydrogen atom; a halogen atom; a cyano group; a nitro group; a $C_1$–$C_6$ alkyl group; a $C_1$–$C_6$ alkylcarbonyl group; a carboxyl group; a $C_1$–$C_{12}$ alkoxycarbonyl group; a phenylcarbonyl group; a phenylcarbonyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; a benzylcarbonyl group; a benzylcarbonyl group having, on the ring thereof, at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; or —CON($R^{17}$)$R^{18}$ (in this formula, $R^{17}$ and $R^{18}$ which may be the same or different represent a hydrogen atom; a $C_1$–$C_6$ alkyl group; a phenyl group; a phenyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; a pyridyl group; a pyridyl group having at least one, the same or different substituents selected from the group consisting of hydrogen atom, halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; a benzyl group; or a benzyl group having, on the ring thereof, at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group); and n represents an integer of 0 to 4;

or alternatively, (R)n may be linked to an adjacent carbon atom on the benzene ring to form a fused ring comprising a $C_3$–$C_4$ alkylene group or a $C_3$–$C_4$ alkenylene group, which may have at least one, the same or different substituents R (R is as defined above)};

characterized by reacting a benzoic acid represented by the following general formula (II):

(II)

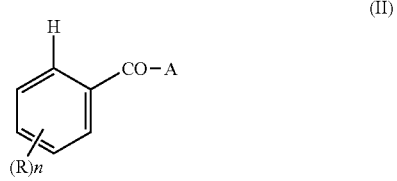

(wherein A, R and n are as defined above), with a halogenating agent in the presence of a palladium catalyst.

MODE FOR CARRYING OUT THE INVENTION

In the definition of the 2-halobenzoic acids of the present invention represented by general formula (I), the term "halogen atom" means a chlorine atom, a bromine atom, an iodine atom or a fluorine atom; "$C_1$–$C_6$ alkyl" means a straight or branched chain alkyl group having 1–6 carbon atoms such as methyl, ethyl, n-propyl, i-propyl, n-butyl, i-butyl, s-butyl, t-butyl, n-pentyl, n-hexyl and the like; "halo $C_1$–$C_6$ alkyl" means a straight or branched chain alkyl group having 1–6 carbon atoms substituted with at least one, the same or different halogen atoms; "$C_3$–$C_4$ alkylene" means a straight or branched chain alkylene group having 3–4 carbon atoms such as propylene, trimethylene, methylpropylene, tetramethylene and the like; "$C_3$–$C_4$ alkenylene" means a straight or branched chain alkenylene group having 3–4 carbon atoms and a double bond in the molecule;

"alkali metal atom" means an alkali metal atom such as sodium, potassium, lithium and the like; and "hetero aryloxy group" means a 6-membered heterocyclic aryloxy group having 1–3 nitrogen atoms on the ring thereof, such as 2-pyridyloxy group, 3-pyridyloxy group, 4-pyridyloxy group, 3-pyridazinylloxy group, 4-pyriazinylloxy group, 2-pyrimidinyloxy group, 4-pyrimidinyloxy group, 5-pyrimidinyloxy group, 2-pyrazinyloxy group, 2-triazinyloxy group and the like.

The process of the present invention for producing 2-halobenzoic acids can be schematically expressed as follows.

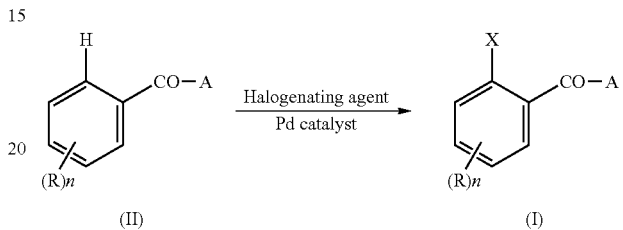

wherein A, R, n and X are as defined above.

That is to say, the 2-halobenzoic acids represented by general formula (I) can be produced by reacting a benzoic acid represented by general formula (II) with various halogenating agents in the presence of a palladium catalyst, in the presence or absence of an appropriate inert solvent.

As the palladium catalyst, for example, divalent palladium compounds such as palladium acetate, palladium chloride, palladium nitrate and the like and palladium complexes obtained by coordinating a ligand such as acetonitrile, triphenylphosphine, benzonitrile or the like to the above-mentioned palladium compounds can be used. These palladium catalysts may be used alone or as a mixture of two or more.

The palladium catalyst is used in a catalytic amount based on the benzoic acid of general formula (II), and usually in an amount of about $1/100,000$ equivalent to $1/2$ equivalent, preferably about $1/100,000$ equivalent to $1/10$ equivalent, and further preferably about $1/10,000$ equivalent to $1/100$ equivalent based on the benzoic acid of general formula (II).

As the halogenating agent which can be used in this reaction, molecular halogens such as $I_2$, $Cl_2$, $Br_2$, ICl and the like and compounds having a halogen atom linked to an element belonging to Group 15 of the periodic table such as N-chlorosuccinimide, N-iodosuccinimide, 1,3-diiodohydantoin, 1,3-diiodo-5,5-dimethylhydantoin and the like can be referred to. The halogenating agent is used in an amount ranging from $1/2$ equivalent to an excessive amount based on the benzoic acid represented by general formula (II), preferably in an amount of about 1 equivalent to about 3 equivalents and further preferably about 1 equivalent to about 1.5 equivalents, based on the benzoic acid of formula (II).

The inert solvent used in this reaction is not particularly limited, unless it greatly obstructs the progress of this reaction. The inert solvents which can be used include organic acid type solvents such as acetic acid and the like; ether type solvents such as dioxane, tetrahydrofuran (THF), diethyl ether and the like; amide type solvents such as dimethylformamide (DMF), dimethylacetamide (DMA), N-methylpyrrolidone and the like; aromatic type solvents such as toluene and the like; ester type solvents such as ethyl acetate and the like; ketone type solvents such as methyl ethyl ketone and the like; halogenated hydrocarbon type solvents such as chloroform, dichloromethane and the like; water; etc. These solvents may be used alone or as a mixture of two or more.

This reaction can be carried out at a temperature ranging from room temperature to boiling point of the used solvent, preferably at a temperature of from about 40° C. to about 200° C., and further preferably at about 50° C. to about 120° C.

In this reaction, a drying agent, a dissolution assistant, a supplementary catalyst, a coordination compound, a metallic salt and the like may be used, according to the need. The additives which can be used include, for example, sodium acetate, copper acetate, benzonitrile, triphenylphosphine, periodic acid, molecular sieves, etc.

EXAMPLES

Next, the present invention is explained more concretely by referring to typical Examples and Comparative Examples. The present invention is by no means limited by these examples.

Example 1

Into a 50 ml-glassreactor were successively introduced 50 mg of palladium acetate, 0.3 g of o-toluic acid and 0.5 g of N-iodosuccinimide, and then 11 ml of DMF. The mixture thus obtained was heated with stirring at 100° C. for 6 hours. After completion of the reaction, the reaction mixture was cooled to room temperature and poured into water, and then the objective product was extracted with ethyl acetate. After separating the mixture into layers, the organic layer was washed successively with aqueous solution of sodium thiosulfate and aqueous solution of sodium chloride and dried over anhydrous magnesium sulfate, and the solvent was distilled off under reduced pressure. Thus, a crude product was obtained.

A part of the crude product obtained above was dissolved in deuterio-DMSO, and its 400 MHz-NMR was measured. As a result, it was found that the starting material was exhaustively consumed and the conversion was 100%. The objective compound, namely 2-iodo-6-methylbenzoic acid, had a purity of 92%.

Regioselectivity of iodination into the 2-position was 100%.

Chemical shifts in $^1$H-NMR ($\delta$): 2.27(3H,s), 7.03(1H,t), 7.26(1H,d), 7.65(1H,d), 11.8(1H,s)

Example 2

Into the same reactor as in Example 1 were successively introduced 50 mg of palladium acetate, 0.3 g of o-toluic acid, 0.36 g of ICl, 0.36 g of sodium acetate, 1 ml of acetic acid and 11 ml of DMF. Then, the mixture thus obtained was heated with stirring at 60° C. for 4 hours. After completion of the reaction, the reaction mixture was cooled to room temperature, and the procedure of Example 1 was repeated to obtain a crude product. The product was analyzed by 400 MHz-NMR in the same manner as in Example 1 to reveal that rate of formation of the objective 2-iodo-6-methylbenzoic acid was 50%.

Regioselectivity of the iodination into the 2-position was 100%.

Example 3

Into the same reactor as in Example 1 were charged 0.07 g of $K_2PdCl_4$, 0.35 g of sodium o-toluate, 0.36 g of ICl, 6 ml of water and 6 ml of dioxane. The mixture thus obtained was heated with stirring at 100° C. for 6 hours. After completion of the reaction, the reaction mixture was cooled to room temperature, poured into water and acidified with dilute hydrochloric acid, and the objective compound was extracted with ethyl acetate. After separating the mixture into phases, the organic layer was washed successively with aqueous solution of sodium thiosulfate and aqueous solution of sodium chloride and dried over anhydrous magnesium sulfate, and the solvent was distilled off under a reduced pressure. Thus, a crude product was obtained.

The same 400 MHz-NMR analysis as in Example 1 revealed that rate of formation of the objective 2-iodo-6-methylbenzoic acid was 40%.

Regioselectivity of iodination into the 2-position was 100%.

Example 4

Into the same reactor as in Example 1 were charged 5 mg of palladium acetate, 0.5 g of mono-n-butyl phthalate, 0.51 g of N-iodosuccinimide and 11 ml of DMF. The mixture thus obtained was heated with stirring at 100° C. for 6 hours. After completion of the reaction, the reaction mixture was cooled to room temperature, and treated in the same manner as in Example 1 to obtain a crude product. The same 400 MHz-NMR analysis as in Example 1 revealed that rate of formation of the objective monobutyl 6-iodophthalate was 45%.

Regioselectivity of iodination into the 6-position was 100%.

Chemical shifts in $^1$H-NMR ($\delta$): 0.88(3H,t), 1.35(2H,q), 1.62(2H,q), 4.18(2H,q), 7.24(1H,t), 7.90(1H,d), 8.05(1H,d), 10.70(1H,s), 12.51(1H,s)

Example 5

Into the same reactor as in Example 1 were charged 50 mg of palladium acetate, 0.3 g of o-toluic acid, 0.28 g of iodine, 0.13 g of periodic acid, 10 ml of acetic acid and 1 ml of water. The mixture thus obtained was heated with stirring at 70° C. for 4 hours. After completion of the reaction, the reaction mixture was cooled and poured into water, and the objective product was extracted with ethyl acetate. After separation into layers, the organic layer was washed successively with aqueous solution of sodium thiosulfate and saturated aqueous solution of sodium chloride and dried over anhydrous magnesium sulfate. By distilling off the solvent under reduced pressure, there was obtained a crude product of the objective compound. The same 400 MHz-NMR analysis as in Example 1 revealed that rate of formation of the objective 2-iodo-6-methylbenzoic acid was 50%.

Regioselectivity of iodination into the 2-position was 100%.

Example 6

Into the same reactor as in Example 1 were charged 50 mg of palladium acetate, 0.3 g of o-toluic acid, 3 g of sodium acetate, 0.36 g of ICl and 11 ml of acetic acid. The mixture thus obtained was heated with stirring at 100° C. for 10 hours. After completion of the reaction, the acetic acid was distilled off under reduced pressure, and the residue was extracted with ethyl acetate. The organic layer was washed successively with aqueous solution of sodium thiosulfate and saturated aqueous solution of sodium chloride and dried over anhydrous magnesium sulfate. By distilling off the solvent under reduced pressure, there was obtained a crude product of the objective compound. The same 400 MHz-NMR analysis as in Example 1 revealed that rate of formation of the objective 2-iodo-6-methylbenzoic acid was 60%.

Regioselectivity of iodination into the 2-position was 100%.

Example 7

Into the same reactor as in Example 1 were charged 82 mg of palladium acetate, 0.5 g of o-toluic acid, 0.49 g of N-chlorosuccinimide and 18 ml of DMF. The mixture thus obtained was heated with stirring at 100° C. for 5 hours. After completion of the reaction, the reaction mixture was cooled and poured into water, and the objective product was extracted with ethyl acetate. After separation into layers, the organic layer was washed successively with aqueous solution of sodium thiosulfate and saturated aqueous solution of sodium chloride and dried over anhydrous magnesium sulfate. By distilling off the solvent under reduced pressure, there was obtained a crude product of the objective compound. The same 400 MHz-NMR analysis as in Example 1 revealed that rate of formation of the objective 2-chloro-6-methylbenzoic acid was 83%.

Regioselectivity of chlorination into the 2-position was 100%.

$^1$H-NMR chemical shift ($\delta$): 2.43(3H,s), 7.13(1H,m), 7.24 (2H,m), 9.15(1H,s)

Example 8

Into the same reactor as in Example 1 were charged 17 mg of palladium acetate, 154 mg of 1,3-diiodo-5,5-dimethylhydantoin, 0.4 g of 2-(1,1-dimethyl-2-methylthioethylaminocarbonyl)-4'-heptafluoroisopropyl-2'-methylbenzanilide and 15 ml of THF. The mixture was heated with stirring at 70° C. for 2.5 hours. After completion of the reaction, the liquid reaction mixture was cooled and poured into water, and the objective product was extracted with ethyl acetate. After separation into layers, the organic layer was washed successively with aqueous solution of sodium thiosulfate and saturated aqueous solution of sodium chloride and dried over anhydrous magnesium sulfate. By distilling off the solvent under reduced pressure, a crude product of the objective compound was obtained. The same 400 MHz-NMR as in Example 1 revealed that rate of formation of the objective 2-(1,1-dimethyl-2-methylthioethylaminocarbonyl)-3-iodo-4'-heptafluoroisopropyl-2'-methylbenzanilide was 88%.

Regioselectivity of the iodination into the 3-position was 100%.

$^1$H-NMR chemical shift ($\delta$): 1.42(6H,s), 1.90(3H,s), 2.39 (3H,s), 2.82(2H,s), 6.10(1H,s), 7.21(1H,t), 7.40(1H,s), 7.45 (1H,d), 7.77(1H,d), 7.98(1H,d), 8.43(1H,d), 8.56(1H,s)

Example 9

Into the same reactor as in Example 1 were charged 10 mg of palladium acetate, 0.27 g of N-chlorosuccinimide, 0.5 g of 2-(4-fluorophenylcarbonyl)-benzoic acid and 20 ml of DMF. The mixture thus obtained was heated with stirring at 70° C. for 3 hours. After completion of the reaction, the reaction mixture was cooled to room temperature and poured into water, and extracted with ethyl acetate. The organic layer was washed successively with aqueous solution of sodium thiosulfate and saturated aqueous solution of sodium chloride and dried over anhydrous magnesium sulfate. By distilling off the solvent under reduced pressure, a crude product of the objective compound was obtained. The same 400 MHz-NMR as in Example 1 revealed that rate of formation of the objective 2-chloro-6-(4-fluorophenylcarbonyl)-benzoic acid was 80%.

$^1$H-NMR chemical shift ($\delta$): 7.09(1H,t), 7.38(1H,d), 7.50 (1H,t), 7.59(1H,m), 7.75(1H,m), 8.09(1H,d), 10.72(1H,s)

Regioselectivity of chlorination into the 2-position was 100%.

Example 10

Into the same reactor as in Example 1 were charged 23 mg of palladium acetate, 0.23 g of N-iodosuccinimide, 0.57 g of 2-(3-(1,1-dimethyl-2-methylthioethylaminocarbonyl)-4'-heptafluoroisopropyl- 2'-methyl)-naphthoanilide and 20 ml of DMF. The mixture thus obtained was heated with stirring at 70° C. for 2 hours. After completion of the reaction, the reaction mixture was cooled to room temperature and poured into water, and the objective product was extracted with ethyl acetate. The organic layer was washed successively with aqueous solution of sodium thiosulfate and saturated aqueous solution of sodium chloride and dried over anhydrous magnesium sulfate. By distilling off the solvent under reduced pressure, a crude product of the objective compound was obtained. Purification of the crude product by silica gel column chromatography (ethyl acetate/n-hexane=1/8) gave 0.57 g of 1-iodo-2-(1,1-dimethyl-2-methylthioethylaminocarbonyl)-4'-heptafluoroisopropyl-2'-methyl-3-naphthoanilide (yield 70%, melting point 228–230° C.).

Regioselectivity of iodination into the 1-position was 100%.

Example 11

Into the same reactor as in Example 1 were charged 14 mg of palladium acetate, 0.23 g of N-iodosuccinimide, 0.34 g of 2-(1,1-dimethyl-2-methylthioethylaminocarbonyl)-4-chloro-4'-heptafluoroisopropyl-2'-methylbenzanilide and 10 ml of DMF. The mixture thus obtained was heated with stirring at 70° C. for 2 hours.

After completion of the reaction, the reaction mixture was cooled to room temperature and poured into water, and the objective product was extracted with ethyl acetate. The organic layer was washed successively with aqueous solution of sodium thiosulfate and saturated aqueous solution of sodium chloride and dried over anhydrous magnesium sulfate. By distilling off the solvent under reduced pressure, a crude product was obtained. Purification of the crude product by silica gel column chromatography (ethyl acetate/n-hexane=1/8) gave 0.32 g of 2-(1,1-dimethyl-2-methylthioethylaminocarbonyl)-3-iodo-4-chloro-4'-heptafluoroisopropyl-2'-methylbenzanilide (yield 78%, melting point 225° C.).

Regioselectivity of iodination into the 3-position was 100%.

Example 12

Into the same reactor as in Example 1 were charged 2 mg of palladium acetate, 1.72 g of 1,3-diiodo-5,5-dimethylhydantoin, 4.8 g of 2-(1,1-dimethyl-2-methylsulfinylethylaminocarbonyl)-4'-heptafluoroisopropyl-2'-methylbenzanilide and 90 ml of THF. The mixture thus obtained was heated with stirring at 70° C. for 5 hours. After completion of the reaction, the reaction mixture was cooled to room temperature and poured into water, and the objective product was extracted with ethyl acetate. The organic layer was washed successively with aqueous solution of sodium thiosulfate and saturated aqueous solution of sodium chloride and dried over anhydrous magnesium sulfate. By distilling off the solvent under reduced pressure, a crude product was obtained. Purification of the crude product by silica gel column chromatography (ethyl acetate/n-hexane=1/3) gave 5.5 g of 3-iodo-2-(1,1-dimethyl-2-methylsulfinylethylaminocarbonyl)-4'-heptafluoroisopropyl-2'-methylbenzanilide (yield 92%).

Regioselectivity of iodination into the 3-position was 100%.

$^1$H-NMR chemical shift (δ): 1.60(6H,d), 2.21(3H,s), 2.38 (3H,s), 2.85(1H,d), 3.10(1H,d), 6.68(1H,s), 7.22(1H,t), 7.42 (1H,s), 7.48(1H,d), 7.78(1H,d), 8.00(1H,d), 8.43(1H,d), 8.45(1H,s)

Example 13

Into the same reactor as in Example 1 were charged 1.5 mg of palladium acetate, 0.83 g of 1,3-diiodo-5,5-dimethylhydantoin, 1.0 g of methyl 2-(1,1-dimethyl-2-methylsulfinylethylaminocarbonyl)benzoate and 5 ml of N-methylpyrrolidone. The mixture thus obtained was heated with stirring at 90° C. for 2 hours. After completion of the reaction, the reaction mixture was cooled to room temperature and poured into water, and the objective product was extracted with ethyl acetate. The organic layer was washed successively with aqueous solution of sodium thiosulfate and saturated aqueous solution of sodium chloride and dried over anhydrous magnesium sulfate. By distilling off the solvent under reduced pressure, a crude product was obtained. Purification of the crude product by silica gel column chromatography (ethyl acetate/n-hexane=1/3) gave 1.27 g of methyl 3-iodo-2-(1,1-dimethyl-2-methylsulfinylethylaminocarbonyl)-benzoate (yield 89.1%, melting point 150.7–151.8° C.).

Regioselectivity of iodination into the 3-position was 100%.

Example 14

Into the same reactor as in Example 1 were charged 5 mg of palladium acetate, 0.3 g of o-toluic acid, 0.5 g of N-iodosuccinimide and 11 ml of DMF. The mixture thus obtained was heated with stirring at 100° C. for 6 hours. After completion of the reaction, the reaction mixture was cooled to room temperature and poured into water, and the objective product was extracted with ethyl acetate. The mixture was separated into layers, the organic layer was washed successively with aqueous solution of sodium thiosulfate and aqueous solution of sodium chloride and dried over anhydrous magnesium sulfate, and then the solvent was distilled off under reduced pressure to obtain a crude product. A part of the crude product was dissolved in DMSO-$d_6$ and analyzed by 400 MHz-NMR. As the result, rate of formation of the objective 2-iodo-6-methylbenzoic acid was found to be 79%.

Regioselectivity of iodination into the 2-position was 100%.

Example 15

Into the same reactor as in Example 1 were charged 0.10 g of palladium acetate, 0.40 g of 2-methyl-2'-methylsulfinylbenzanilide, 0.33 g of 1,3-diiodo-5,5-dimethylhydantoin and 5 ml of N,N-dimethylacetamide. The mixture thus obtained was stirred at 90° C. for 2 hours. After cooling to room temperature, the reaction mixture was filtered with Celite, and the filtrate was poured into saturated aqueous solution of sodium thiosulfate and extracted with ethyl acetate. The organic layer was washed with 0.1N-aqueous hydrochloric acid and dried over anhydrous sodium sulfate, and the solvent was distilled off under reduced pressure. The concentrate thus obtained was purified by silica gel dry column chromatography (hexane/ethyl acetate=1/2). Thus, 0.43 g (yield 72%) of 2-iodo-6-methyl-2'-methylsulfinylbenzanilide was obtained. Regioselectivity of iodination into the 2-position was 100%.

$^1$H-NMR (CDCl$_3$, ppm, δ): 2.45(3H,s), 3.00(3H,s), 6.99 (1H,dd), 7.18–7.25(2H,m), 7.33(1H,dd), 7.57(1H,dd), 7.66 (1H,d), 8.72(1H,d), 10.62(1H,bs)

Example 16

2-Methyl-2'-nitrobenzanilide was treated in the same manner as in Example 15 to obtain 2-iodo-6-methyl-2'-nitrobenzanilide (yield 39%, melting point 114.8° C.). Regioselectivity of iodination into the 2-position was 100%.

Example 17

2,4-Dimethylbenzanilide was treated in the same manner as in Example 15 to obtain 2-iodo-4,6-dimethylbenzanilide (yield 17%). Regioselectivity of iodination into the 2-position was 100%.

$^1$H-NMR (CDCl$_3$, ppm, δ): 2.29(3H,s), 2.40(3H,s), 7.03 (1H,s), 7.18(1H,ddd), 7.28(1H,bs), 7.39(2H,dd), 7.52(1H,s), 7.63(2H,dd)

Example 18

2,4-Dimethyl-2'-methylsulfonylbenzanilide was treated in the same manner as in Example 15 to obtain 2-iodo-4,6-dimethyl-2'-methylsulfonylbenzanilide (yield 14%). Regioselectivity of iodination into the 2-position was 100%.

$^1$H-NMR (CDCl$_3$, ppm, δ) 2.29(3H,s), 2.39(3H,s), 3.16(s), 7.02(1H,ss), 7.26(1H,dd), 7.51(1H,s), 7.71(1H,ddd), 7.95(1H,dd), 8.70(1H,dd), 9.56(1H,bs)

Example 19

2,4-Dimethyl-2'-methylsulfinylbenzanilide was treated in the same manner as in Example 15, except that the amount of palladium acetate was decreased to 3.3 mg, to obtain 2-iodo-4,6-dimethyl-2'-methylsulfinyl-benzanilide (yield 36%, melting point 113.6° C.). Regioselectivity of iodination into the 2-position was 100%.

Example 20

N-(1,1-Dimethyl-2-methylthioethyl)-2-nitrobenzamide was treated in the same manner as in Example 19, except that N-iodosuccinimide was used as the iodinating agent, to obtain N-(1,1-dimethyl-2-methylthioethyl)-2-iodo-6-nitrobenzamide (yield 43%, melting point 114–115° C.). Regioselectivity of iodination into the 2-position was 100%.

Example 21

2-(1,1-Dimethyl-2-methylsulfinylethylaminocarbonyl)-N-(6-(1,1,1,3,3,3-hexafluoropropan-2-yloxy)-2-methylpyridin-3-yl)benzamide was treated in the same manner as in Example 19 to obtain 2-(1,1-dimethyl-2-methylsulfinylethlaminocarbonyl)-N-(6-(1,1,1,3,3,3-hexafluoropropane-2-yloxy)-2-methylpyridin-3-yl)-3-iodobenzamide (yield 98%). Regioselectivity of iodination into the 3-position was 100%.

$^1$H-NMR (CDCl$_3$, ppm, δ) 1.61(3H,s), 1.64(3H,s), 2.36 (3H,s), 2.44(3H,s), 2.98(1H,d), 3.13(1H,d), 6.53(1H,m), 6.82(2H,m), 7.16(1H,t), 7.73(1H,d), 7.95(1H,d), 8.27(1H, d), 8.44(1H,s)

Example 22

2-(1,1-Dimethyl-2-methylthioethylaminocarbonyl)-4-fluoro-4'-heptafluoroisopropyl-2'-methylbenzanilide was treated in the same manner as in Example 20, except that the amount of palladium acetate was altered to 33 mg and the reaction temperature was altered to 70° C., to obtain 2-(1, 1-dimethyl-2-methylthioethylaminocarbonyl)-4-fluro-4'-heptafluoroisopropyl-3-iodo-2'-methylbenzanilide (yield 79%, melting point 218–220° C.). Regioselectivity of iodination into the 3-position was 100%.

Example 23

5-Chloro-2-(1,1-dimethyl-2-methylthioethylaminocarbonyl)-4'-heptafluoroisopropyl-2'-methylbenzanilide was treated in the same manner as in Example 22 to obtain 5-chloro-2-(1,1-dimethyl-2-methylthioethylaminocarbonyl)-4'-heptafluoroisopropyl-3-iodo-2'-methylbenzanilide (yield 80%, melting point 227° C.). Regioselectivity of iodination into the 3-position was 100%.

Example 24

5-Bromo-2-(1,1-dimethyl-2-methylthioethylaminocarbonyl)-4'-heptafluoroisopropyl-2'-methylbenzanilide was treated in the same manner as in Example 22 to obtain 5-bromo-2-(1,1-dimethyl-2-methylthioethylaminocarbonyl)-4'-heptafluoroisopropyl- 3-iodo-2'-methylbenzanilide (yield 75%, melting point 205–207° C.). Regioselectivity of iodination into the 3-position was 100%.

Example 25

2-(1,1-Dimethyl-2-methylthioethylaminocarbonyl)-4'-heptafluoroisopropyl-2',5-dimethylbenzanilide was treated in the same manner as in Example 22 to obtain 2-(1,1-dimethyl-2-methylthioethylaminocarbonyl)-4'-heptafluoroisopropyl-3-iodo-2',5-dimethylbenzanilide (yield 48%, melting point 234–235° C.). Regioselectivity of iodination into the 3-position was 100%.

Example 26

2-(1,1-Dimethyl-2-methylthioethylaminocarbonyl)-4'-heptafluoroisopropyl-4-methoxy-2'-methylbenzanilide was treated in the same manner as in Example 22 to obtain 2-(1,1-dimethyl-2-methylthioethylaminocarbonyl)-4'-heptafluoroisopropyl-3-iodo-4-methoxy-2'-methylbenz-anilide (yield 84%, melting point 153–155° C.). Regioselectivity of iodination into the 3-position was 100%.

Example 27

2-(1,1-Dimethyl-2-methylthioethylaminocarbonyl)-4'-heptafluoroisopropyl-2'-methyl-4-trifluoromethoxybenzanilide was treated in the same manner as in Example 22 to obtain 2-(1,1-dimethyl-2-methylthioethylaminocarbonyl)-4'-heptafluorisopropyl-3-iodo-2'-methyl-4-trifluoromethoxybenzanilide (yield 86%, melting point 213–214° C.). Regioselectivity of iodination into the 3-position was 100%.

Example 28

3-(1,1-Dimethyl-2-methylthioethylaminocarbonyl)-4'-heptafluoroisopropyl-2'-methyl-2-naphthalenecarboxylic acid anilide was treated in the same manner as in Example 22 to obtain 2-(1,1-dimethyl-2-methylthioethylaminocarbonyl)-4'-heptafluoroisopropyl-1-iodo-2'-methyl-3-naphthalenecarboxylic acid anilide (yield 70%, melting point 228–230° C.). Regioselectivity of iodination into the 1-position was 100%.

Example 29

2'-Methyl-8-(1-methyl-2-methylthioethylaminocarbonyl)-4'-trifluoromethoxy-1-naphthalenecarboxylic acid anilide was treated in the same manner as in Example 22 to obtain 7-iodo-2'-methyl-8-(1-methyl-2-methylthioethylaminocarbonyl)-4'-trifluoromethoxy-1-naphthalenecarboxylic acid anilide (yield 75%, melting point 176–178° C.). Regioselectivity of iodination into the 1-position was 100%.

Example 30

2-(4-Chloro-2-methylphenoxy)-N-(1,1-dimethyl-2-methylthioethyl)benzamide was treated in the same manner as in Example 22 to obtain 2-(4-chloro-2-methylphenoxy)-N-(1, 1-dimethyl-2-methylthioethyl)-6-iodobenzamide (yield 85%, melting point 128–130° C.). Regioselectivity of iodination into the 6-position was 100%.

Example 31

2-(3-Chloro-5-trifluoromethylpyridin-2-yloxy)-N-(1,1-dimethyl-2-methylthioethyl)benzamide was treated in the same manner as in Example 22 to obtain 2-(3-chloro-5-trifluoromethylpyridin-2-yloxy)-N-(1,1-dimethyl-2-methylthioethyl)-6-iodobenzamide (yield 81%, melting point 83–85° C.). Regioselectivity of iodination into the 6-position was 100%.

Example 32

2-(4,6-dimethoxypyrimidin-2-yloxy)-N-(1,1-dimethyl-2-methylthioethyl)benzamide was treated in the same manner as in Example 22 to obtain 2-(4,6-dimethoxypyrimidin-2-yloxy)-N-(1,1-dimethyl-2-methylthioethyl)-6-iodobenzamide (yield 89%, refractive index 1.5765 at 21.0° C.). Regioselectivity of iodination into the 6-position was 100%.

Example 33

N-(1,1-Dimethyl-2-methylthioethyl)-2-(4-trifluoromethylphenyl)benzamide was treated in the same manner as in Example 22 to obtain N-(1,1-dimethyl-2-methylthioethyl)-6-iodo-2-(4-trifluoromethylphenyl)benzamide (yield 61%, melting point 194–196° C.). Regioselectivity of iodination into the 6-position was 100%.

Example 34

N-(1,1-Dimethyl-2-methylsulfinylethyl)-2-(4-trifluoromethylphenyl)benzamide was treated in the same manner as in Example 22, except that the amount of palladium acetate was decreased to 3.3 mg, to obtain N-(1,1-dimethyl-2-methylsulfinylethyl)-6-iodo-2-(4-trifluoromethylphenyl)benzamide (yield 64%, melting point 155–158° C.). Regioselectivity of iodination into the 6-position was 100%.

Example 35

2-(1,1-Dimethyl-2-(N-methoxyimino)ethylaminocarbonyl)-4'-(1,1,2,3,3,3-hexafluoropropan-1-yloxy)-2'-methylbenzanilide was treated in the same manner as in Example 22, except that the amount of palladium acetate was altered to 67 mg and the reaction temperature was altered to 90° C., to obtain 2-(1,1-dimethyl)-2-(N-methoxyimino)ethylaminocarbonyl)-4'-(1,1,2,3,3,3-hexafluoropropan-1-yloxy)-3-iodo-2'-methylbenzanilide (yield 78%, melting point 188° C.). Regioselectivity of iodination into the 3-position was 100%.

Example 36

Into the same reactor as in Example 1 were charged 0.17 g of palladium acetate, 0.40 g of 2-(1,1-dimethyl-2-(N-methoxyimino)ethylaminocarbonyl)-4'-heptafluoroisopropyl-2'-methylbenzanilide, 0.15 g of N-bromo-succinimide and 5 ml of tetrahydrofuran. The mixture was heated under reflux with stirring for 2 hours. After allowing the reaction mixture to cool, the solvent was distilled off under reduced pressure, the concentrate thus obtained was purified by silica gel dry column chromatography (hexane/ethyl acetate=1/1) to obtain 0.31 g of 3-bromo-2-(1,1-dimethyl-2-(N-methoxyimino)-ethylaminocarbonyl)-4'-heptafluoroisopropyl-2'-methylbenzanilide (yield 67%, melting point 242.5° C.). Regioselectivity of bromination into the 3-position was 100%.

Example 37

2-(1,1-Dimethyl-2-(N-methoxyimino)ethylaminocarbonyl)-2'-methyl-4'-trifluoromethoxybenzanilide was treated in the same manner as in Example 36, except that the N-bromosuccinimide was replaced with N-chlorosuccinimide, to obtain 3-chloro-2-(1,1-dimethyl-2-(N-methoxyimino)ethylaminocarbonyl)-2'-methyl-4'-trifluoromethoxybenzanilide (yield 63%, melting point 197° C.). Regioselectivity of chlorination into the 3-position was 100%.

Example 38

2-(2-(N-methoxyimino)ethylaminocarbonyl)-2'-methyl-4'-pentafluoroethylbenzanilide was treated in the same manner as in Example 36, except that the N-bromosuccinimide was replaced with N-iodosuccinimide, to obtain 3-iodo-2-(2-(N-methoxyimino)ethylaminocarbonyl)-2'-methyl-4'-pentafluoroethylbenzanilide (yield 53%, melting point 110° C.). Regioselectivity of iodination into the 3-position was 100%.

Example 39

2-(1,1-Dimethyl-2-(N-methoxyimino)ethylaminocarbonyl)-N-(6-(1,1,1,3,3,3-hexafluoropropan-2-yloxy)-2-methylpyridin-3-yl)benzamide was treated in the same manner as in Example 36, except that the N-bromosuccinimide was replaced with N-iodosuccinimide, to obtain 2-(1,1-dimethyl-2-(N-methoxyimino)ethylaminocarbonyl)-N-(6-(1,1,1,3,3,3-hexafluoropropan-2-yloxy)-2-methylpyridin-3-yl)-3-iodobenzamide (yield 83%, melting point 220° C.). Regioselectivity of iodination into the 3-position was 100%.

Example 40

2-(2-(N,N-Dimethylaminocarbonyl)-1-methylethylaminocarbonyl)-2'-methyl-4'-trifluoromethoxybenzanilide was treated in the same manner as in Example 39 to obtain 2-(2-(N,N-dimethylaminocarbonyl)-1-methylethylaminocarbonyl)-3-iodo-2'-methyl-4'-trifluoromethoxybenzanilide (yield 40%, melting point 104° C.). Regioselectivity of iodination into the 3-position was 100%.

Example 41

Into the same reactor as in Example 1 were charged 1.32 mg of palladium acetate, 0.78 g of 1,3-diiodo-5,5-dimethylhydantoin, n-butyl 2-(1,1-dimethyl-2-methylsulfinylethylaminocarbonyl)benzoate and 5 ml of N,N-dimethylacetamide. After stirring the mixture at 90° C. for 30 minutes, 0.56 g of 1,3-diiodo-5,5-dimethylhydantoin was added, and the mixture thus obtained was stirred at 90° C. for 3.5 hours. After completion of the reaction, the solvent was distilled off under reduced pressure, an aqueous solution of sodium thiosulfate was added, and the mixture thus obtained was extracted twice with toluene. The organic layer was washed successively with 0.5N aqueous hydrochloric acid, an aqueous solution of sodium bicarbonate and a saturated aqueous solution of sodium chloride. The organic layer was dried over anhydrous sodium sulfate, and the solvent was distilled off under reduced pressure. The crude product thus obtained was washed with hexane-ether mixture to obtain 2.26 g of n-butyl 2-(1,1-dimethyl-2-methylsulfinylethylaminocarbonyl)-3-iodobenzoate (yield 82%, melting point 57.5–66.3° C.). Regioselectivity of iodination into the 3-position was 100%.

Comparative Example 1

According to the method described in the Reference literature (7) J. Org. Chem., 1998, 63, 5211, 22 mg of palladium acetate, 0.12 g of benzoic acid, 20 mg of copper acetate, 0.4 g of Molecular Sieves 4A, 5 ml of DMF and 0.75 g of iodine (in place of the styrene, which was used in the literature shown above) were charged and heated with stirring at 100° C. for 8 hours. After completion of the reaction, the reaction mixture was cooled and poured into water, and the objective product was extracted with ethyl acetate. After separating the mixture into layers, the organic layer was dried over anhydrous magnesium sulfate and the solvent was distilled off under reduced pressure. Thus, the objective compound was obtained as a crude product. The same 400 MHz-NMR as in Example 1 revealed that the rate of formation of the objective 2-iodobenzoic acid was 10%.

$^1$H-NMR chemical shift (δ): 7.35(1H,t), 7.49(1H,t), 7.72(1H,d), 7.99(1H,d), 10.32(1H,s)

Comparative Example 2

A reaction was carried out under the reaction conditions described in the Reference literature (7) J. Org. Chem., 1998, 63, 5211, except that the molar ratios were the same as in Example 13. Thus, 5 mg of palladium acetate, 0.3 g of o-toluic acid, 4.4 mg of copper acetate, 0.5 g of N-iodosuccinimide, 0.4 g of Molecular Sieves 4A and 11 ml of DMF were charged and heated with stirring at 100° C. for 6 hours. After completion of the reaction, the reaction mixture was cooled and poured into water, and the objective compound was extracted with ethyl acetate. After separating the reaction mixture into layers, the organic layer was dried over anhydrous magnesium sulfate and the solvent was distilled off under reduced pressure. Thus, a crude product was obtained. The same 400 MHz-NMR as in Example 1 revealed that no formation of the objective 2-iodobenzoic acid was observed, and the substances recovered were 10% of a substance having an unknown structure and 90% of the starting material.

As shown in Comparative Examples 1 and 2, the iodination (halogenation) does not progress at all or progresses to give only a very low yield of product so far as the method described in the Reference literature (7) is adopted, demonstrating that the method of the present invention is clearly superior to, as a method of halogenation.

What is claimed is:
1. A process for producing a 2-halobenzoic acid represented by the following formula (I):

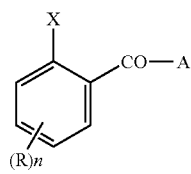

{wherein X represents a chlorine atom, a bromine atom or an iodine atom;

A represents —OH, —OM (in this formula, M represents an alkali metal atom) or —N($R^6$)$R^7$ (in this formula, $R^6$ and $R^7$ which may be the same or different represent a hydrogen atom; a $C_1$–$C_6$ alkyl group; a phenyl group; a phenyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group, halo $C_1$–$C_6$ alkoxy group, $C_1$–$C_6$ alkylsulfinyl group and $C_1$–$C_6$ alkylsulfonyl group; a group represented by the following formula:

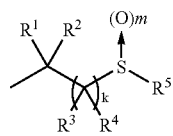

(in this formula, $R^1$, $R^2$, $R^3$ and $R^4$ which may be the same or different represent a hydrogen atom or a $C_1$–$C_6$ alkyl group, $R^5$ represents a $C_1$–$C_6$ alkyl group, m represents an integer of 0 or 1, and k represents an integer of 1 or 2); a group represented by the following formula:

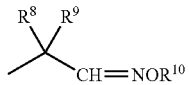

(in this formula, $R^8$, $R^9$ and $R^{10}$ which may be the same or different represent a hydrogen atom or a $C_1$–$C_6$ alkyl group); or a group represented by the following formula:

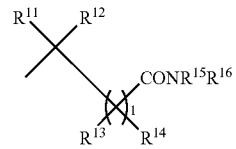

(in this formula, $R^{11}$, $R^{12}$, $R^{13}$, $R^{14}$, $R^{15}$ and $R^{16}$ which may be the same or different represent a hydrogen atom or a $C_1$–$C_6$ alkyl group and l represents an integer of 1 or 2));

R which may be the same or different represents a hydrogen atom; a halogen atom; a cyano group; a nitro group; a $C_1$–$C_6$ alkyl group; a $C_1$–$C_6$ alkylcarbonyl group; a carboxyl group; a $C_1$–$C_{12}$ alkoxycarbonyl group; a phenylcarbonyl group; a phenylcarbonyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; a benzylcarbonyl group; a benzylcarbonyl group having, on the ring thereof, at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; or —CON($R^{17}$)$R^{18}$ (in this formula, $R^{17}$ and $R^{18}$ which may be the same or different represent a hydrogen atom; a $C_1$–$C_6$ alkyl group; a phenyl group; a phenyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; a pyridyl group; a pyridyl group having at least one, the same or different substituents selected from the group consisting of hydrogen atom, halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; a benzyl group; or a benzyl group having, on the ring thereof, at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group); and n represents an integer of 0 to 4;

or alternatively (R)n may be linked to an adjacent carbon atom on the benzene ring to form a fused ring being a $C_3$–$C_4$ alkylene group or a $C_3$–$C_4$ alkenylene group, which may have at least one, the same or different substituents R (R is as defined above)};

characterized by reacting a benzoic acid represented by the following formula (II):

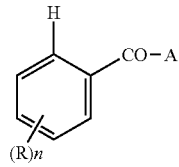

(II)

(wherein A, R and n are as defined above), with a halogenating agent in the presence of a palladium catalyst.

2. A process according to claim 1, wherein A represents —OH or —OM (in this formula, M represents an alkali metal atom).

3. A process for producing a 2-halobenzoic acid represented by the following formula (I):

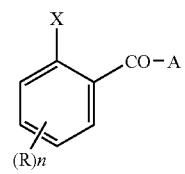

(I)

{wherein X represents a chlorine atom, a bromine atom or an iodine atom;

A represents —N(R$^6$)R$^7$ (in this formula, R$^6$ and R$^7$ may be the same or different and represent a hydrogen atom; a $C_1$–$C_6$ alkyl group; a phenyl group; a phenyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group, halo $C_1$–$C_6$ alkoxy group, $C_1$–$C_6$ alkylsulfinyl group and $C_1$–$C_6$ alkylsulfonyl group; or

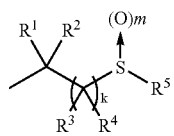

(in this formula, R$^1$, R$^2$, R$^3$ and R$^4$ may be the same or different and represent a hydrogen atom or a $C_1$–$C_6$ alkyl group, R$^5$ represents a $C_1$–$C_6$ alkyl group, m represents an integer of 0 or 1, and k represents an integer of 1 or 2));

R which may be the same or different represents a hydrogen atom; a halogen atom; a cyano group; a nitro group; a $C_1$–$C_6$ alkyl group; a $C_1$–$C_6$ alkylcarbonyl group; a carboxyl group; a $C_1$–$C_{12}$ alkoxycarbonyl group; a phenylcarbonyl group; a phenylcarbonyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; a benzylcarbonyl group; a benzylcarbonyl group having, on the ring thereof, at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; or —CON(R$^{17}$)R$^{18}$ (in this formula, R$^{17}$ and R$^{18}$ which may be the same or different represent a hydrogen atom; a $C_1$–$C_6$ alkyl group; a phenyl group; a phenyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; a pyridyl group; a pyridyl group having at least one, the same or different substituents selected from the group consisting of hydrogen atom, halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group; a benzyl group; or a benzyl group having, on the ring thereof, at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group and halo $C_1$–$C_6$ alkoxy group); and n represents an integer of 0 to 4;

or alternatively (R)n may be linked to an adjacent carbon atom on the benzene ring to form a fused ring being a $C_3$–$C_4$ alkylene group or a $C_3$–$C_4$ alkenylene group, which may have at least one, the same or different substituents R (R is as defined above)};

characterized by reacting a benzoic acid represented by the following formula (II):

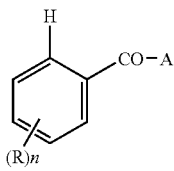

(II)

(wherein A, R and n are as defined above), with a halogenating agent in the presence of a palladium catalyst.

4. A process according to claim 3, wherein R$^6$ and R$^7$ may be the same or different and represent a hydrogen atom or

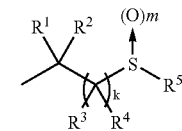

(in this formula, R$^1$, R$^2$, R$^3$ and R$^4$ may be the same or different and represent a hydrogen atom or a $C_1$–$C_6$ alkyl group, R$^5$ represents a $C_1$–$C_6$ alkyl group, m represents an integer of 0 or 1, and k represents an integer of 1 or 2).

5. A process according to claim 3, wherein R$^6$ and R$^7$ may be the same or different and represent a hydrogen atom; a phenyl group; or a phenyl group having at least one, the same or different substituents selected from the group consisting of halogen atom, cyano group, nitro group, $C_1$–$C_6$ alkyl group, $C_1$–$C_6$ alkoxy group, halo $C_1$–$C_6$ alkyl group, halo $C_1$–$C_6$ alkoxy group, $C_1$–$C_6$ alkylsulfinyl group and $C_1$–$C_6$ alkylsulfonyl group.

* * * * *